(12) United States Patent
Naidu

(10) Patent No.: US 11,338,122 B2
(45) Date of Patent: May 24, 2022

(54) WINGED NEEDLE SET SECUREMENT

(71) Applicant: Becton, Dickinson and Company, Franklin Lakes, NJ (US)

(72) Inventor: Jithendra Kumar Sathyanarayana Naidu, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/830,912

(22) Filed: Mar. 26, 2020

(65) Prior Publication Data

US 2020/0306504 A1 Oct. 1, 2020

Related U.S. Application Data

(60) Provisional application No. 62/824,787, filed on Mar. 27, 2019.

(51) Int. Cl.
*A61M 39/04* (2006.01)
*A61M 25/06* (2006.01)
(Continued)

(52) U.S. Cl.
CPC ............ *A61M 39/04* (2013.01); *A61M 5/162* (2013.01); *A61M 25/0606* (2013.01); *A61M 25/0625* (2013.01); *A61M 25/0637* (2013.01); *A61M 39/10* (2013.01); *A61M 39/1011* (2013.01); *A61M 25/0693* (2013.01)

(58) Field of Classification Search
CPC ...... A61M 2039/1027; A61M 25/0637; A61M 2039/1072; A61M 39/1011; A61M 39/04; A61M 25/0625; A61M 25/0606; A61M 25/0693; A61M 39/10; A61M 25/0097; A61M 5/162; A61M 25/065; A61M 2039/1077; A61M 2039/1033
See application file for complete search history.

(56) References Cited

U.S. PATENT DOCUMENTS 2,546,672 A * 3/1951 Sprankl .................. F16N 21/02
184/105.3
4,219,912 A * 9/1980 Adams ................. B29C 66/5344
604/86
(Continued)

FOREIGN PATENT DOCUMENTS

| CN | 107088243 A | * | 8/2017 |
| WO | 93/03777 | | 3/1993 |
| WO | 2007/052278 | | 5/2007 |

*Primary Examiner* — William R Carpenter
(74) *Attorney, Agent, or Firm* — Kirton McConkie; Whitney Blair; Kevin Stinger

(57) ABSTRACT

A connector to secure a winged needle set to a catheter assembly may include a male luer lock. The male luer lock may include a tapered male discharge nozzle and a locking ring surrounding the tapered male discharge nozzle. The locking ring may be internally threaded. The connector may include a septum configured to prevent flow through the tapered male discharge nozzle. The connector may include an arm, which may include a first end, a second end, and a hinge portion disposed between the first end and the second end. The first end may be coupled to the male luer lock. In response to the hinge portion moving from an open position to a closed position, the arm may be configured to secure the winged needle set to the connector.

15 Claims, 8 Drawing Sheets

(51) Int. Cl.
*A61M 5/162* (2006.01)
*A61M 39/10* (2006.01)

(56) References Cited

U.S. PATENT DOCUMENTS

| | | | | |
|---|---|---|---|---|
| 4,809,679 | A | * | 3/1989 | Shimonaka ........ A61B 1/00137 600/154 |
| 5,135,489 | A | | 8/1992 | Jepson et al. |
| 5,501,426 | A | * | 3/1996 | Atkinson ............ A61M 39/045 251/149.1 |
| 5,853,094 | A | * | 12/1998 | Tanaka .............. B29C 45/14336 215/247 |
| 6,096,024 | A | * | 8/2000 | Graves ............... A61M 39/1011 604/161 |
| 6,171,287 | B1 | * | 1/2001 | Lynn ..................... A61M 39/02 251/149 |
| 8,066,670 | B2 | * | 11/2011 | Cluff .................... A61M 25/00 604/126 |
| 2002/0173748 | A1 | * | 11/2002 | McConnell ........... A61M 5/162 604/167.02 |
| 2002/0193752 | A1 | * | 12/2002 | Lynn ..................... A61M 39/26 604/249 |
| 2011/0098601 | A1 | * | 4/2011 | Huynh .................. H01R 24/58 600/585 |
| 2013/0079730 | A1 | | 3/2013 | Mosler et al. |

* cited by examiner

WINGED NEEDLE SET SECUREMENT

RELATED APPLICATIONS

This application claims the benefit of U.S. Application No. 62/824,787, filed Mar. 27, 2019, and entitled WINGED NEEDLE SET SECUREMENT, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the vein, a user generally confirms that there is "flashback" of blood in a flashback chamber of a PIVC assembly. Once placement of the needle has been confirmed, a user may temporarily occlude flow in the vein and remove the introducer needle, leaving the PIVC in place within the vein. The PIVC may then be used for fluid infusion and/or blood withdrawal or collection.

The PIVC assembly may include an extension tube and a pro re nata ("PRN") connector. In some instances, a winged needle set may be coupled to the PRN connector to flush the PIVC assembly. The winged needle set may be secured to skin of the patient with tape to help prevent accidental removal of the winged needle set from the PRN connector, which could result in a needle stick.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to connectors to secure a winged needle set to a catheter assembly, as well as related systems and methods. In some embodiments, a connector to secure a winged needle set to a catheter assembly may include a male luer lock. In some embodiments, the male luer lock may include a tapered male discharge nozzle and a locking ring surrounding the tapered male discharge nozzle. In some embodiments, the locking ring may be internally threaded.

In some embodiments, the connector may include a septum configured to prevent flow through the tapered male discharge nozzle. In some embodiments, the connector may include an arm, which may include a first end, a second end, and a hinge portion disposed between the first end and the second end. In some embodiments, the hinge portion may include a living hinge. In some embodiments, the first end may be coupled to the male luer lock. In some embodiments, in response to the hinge portion moving from an open position to a closed position, the arm may be configured to secure a winged needle set to the connector.

In some embodiments, the second end of the arm may include a first prong, a second prong, and an opening disposed between the first prong and the second prong. In some embodiments, the opening may be aligned with the tapered male discharge nozzle in response to the hinge portion being disposed in the closed position. In some embodiments, the first prong may include a first protrusion and/or the second prong may include a second protrusion. In some embodiments, a portion of the opening between the first protrusion and the second protrusion may include a narrowed diameter.

In some embodiments, the locking ring may extend beyond an end of the tapered male discharge nozzle, which may reduce a risk of bacterial contamination of the tapered male discharge nozzle. In some embodiments, the locking ring may include a flange. In some embodiments, the septum may include a cap and/or a stem extending from the cap. In some embodiments, the stem may extend into the tapered male discharge nozzle and/or the cap may rest on the flange, which may facilitate securement of the septum within the connector.

In some embodiments, the stem may include one or more protrusions. In some embodiments, the tapered male discharge nozzle may be spaced apart from the locking ring by a cavity. In some embodiments, the connector may include one or more apertures, which may connect an interior of the tapered male discharge nozzle with the cavity. In some embodiments, the one or more protrusions of the septum may be disposed within the one or more apertures, which may facilitate securement of the septum within the connector.

In some embodiments, the tapered male discharge nozzle may be coupled to the locking ring at an attachment portion. In some embodiments, the one or more apertures may be proximate the attachment portion. In some embodiments, the flange may be disposed between the cap and the one or more protrusions and/or may contact the one or more protrusions.

In some embodiments, a method of securing the winged needle set to the catheter assembly may include coupling the connector to the catheter assembly. In some embodiments, the method may include inserting the winged needle set through the septum and into the tapered male discharge nozzle. In some embodiments, the winged needle set may include a hub, a needle secured within the hub, and a wing extending outwardly from the hub.

In some embodiments, the method may include moving the hinge portion from the open position to the closed position. In some embodiments, in response to the hinge portion being in the closed position, the wing of the winged needle set may be secured between the second end and the septum. In some embodiments, the winged needle set may extend through the opening in response to the hinge portion being in the closed position. In some embodiments, moving the hinge portion from the open position to the closed position may include moving a portion of the winged needle set through the narrowed diameter. In some embodiments, a diameter of the portion of the winged needle set may be greater than the narrowed diameter.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
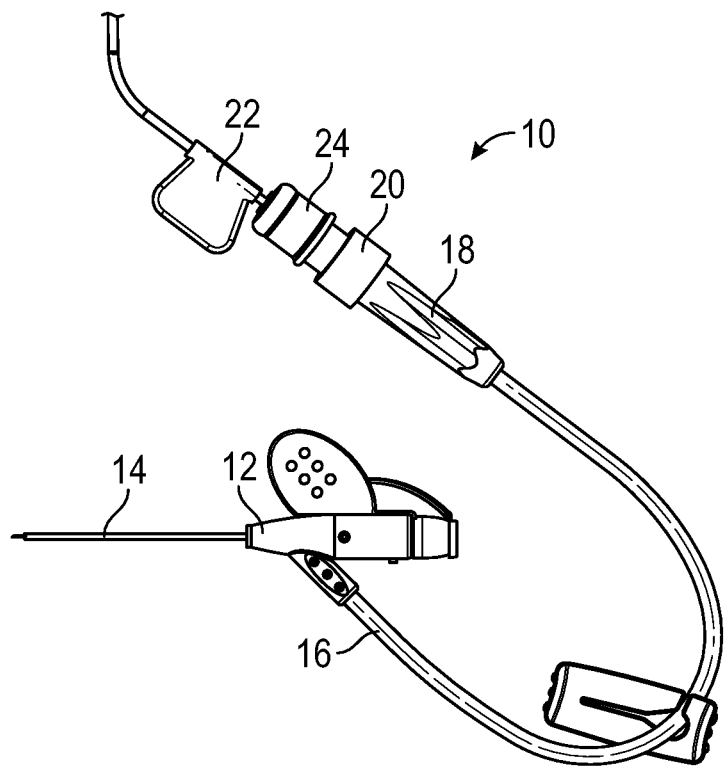
FIG. 1A is an upper perspective view of an example prior art catheter system.
Figure 1B:
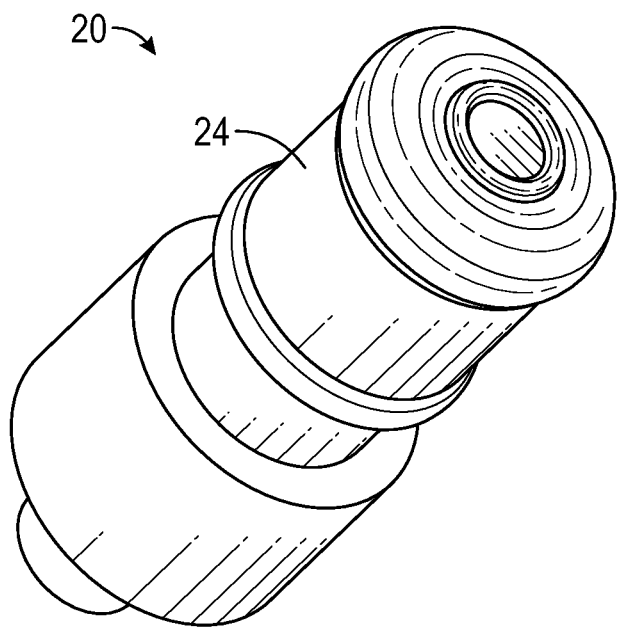
FIG. 1B is an upper perspective view of a prior art connector of the prior art catheter system of FIG. 1A.
Figure 1C:
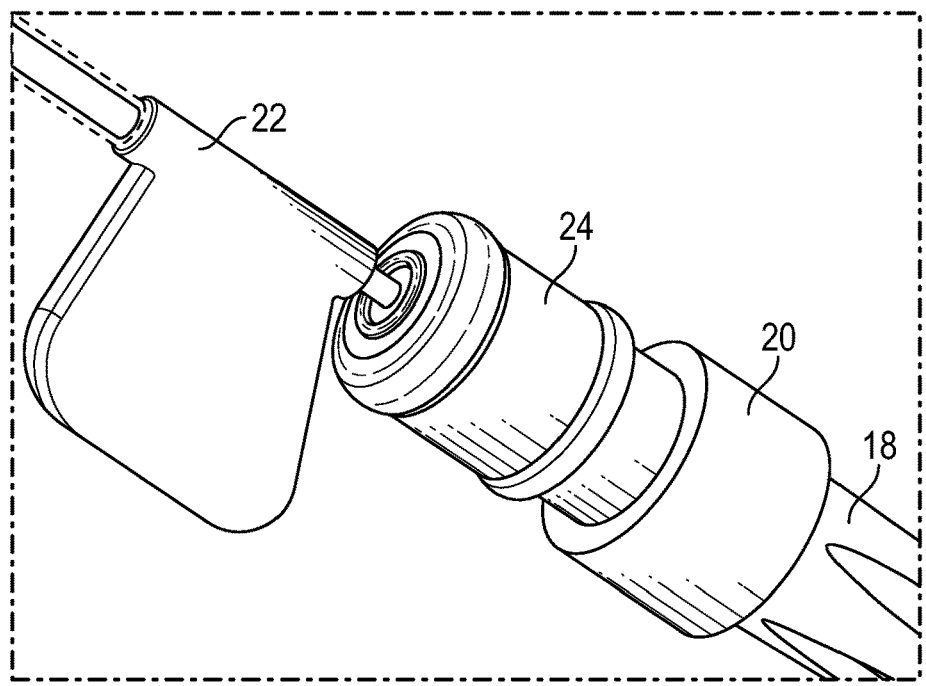
FIG. 1C is an upper perspective view of a prior art winged needle set inserted into the prior art connector of FIG. 1B.

Referring now to FIG. 1A-1C, a prior art catheter system 10 is illustrated. The prior art catheter system 10 includes a catheter adapter 12, a catheter 14 extending distally from the catheter adapter 12, and an extension tube 16 extending proximally from the catheter adapter 12. A proximal end of the extension tube 16 may include an adapter 18. A PRN adapter 20 may be coupled to the adapter 18, and a winged needle set 22 may be inserted through a septum 24 of the PRN adapter 20 to flush the prior art catheter system 10.

Figure 1D:
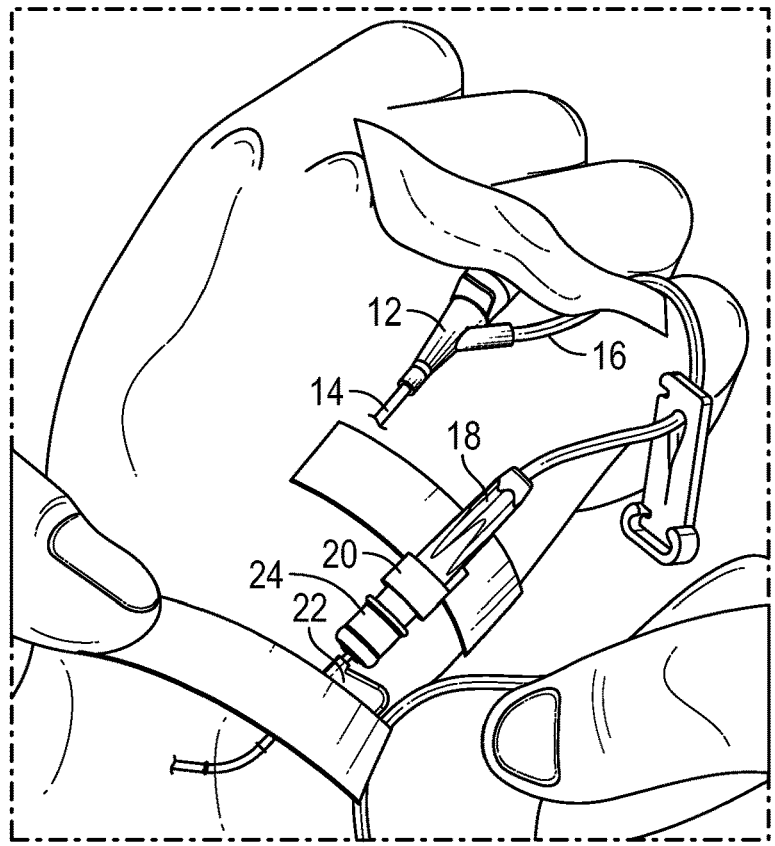
FIG. 1D is an upper perspective view of the prior art catheter system of FIG. 1A adhered to skin of a patient.

Referring now to FIG. 1D, the winged needle set 22 of the prior art catheter system 10 may be secured to skin of the patient with adhesive tape. The adhesive tape may result in skin irritation. Also, application of the adhesive tape to the skin can be time consuming for a clinician. Further, there is a potential for the winged needle set 22 to be accidentally removed from the PRN adapter 20 if the adhesive tape is disturbed or fails. The winged needle set 22 removed from the PRN adapter 20 poses a needle stick risk to a clinician or the patient.

Figure 2A:
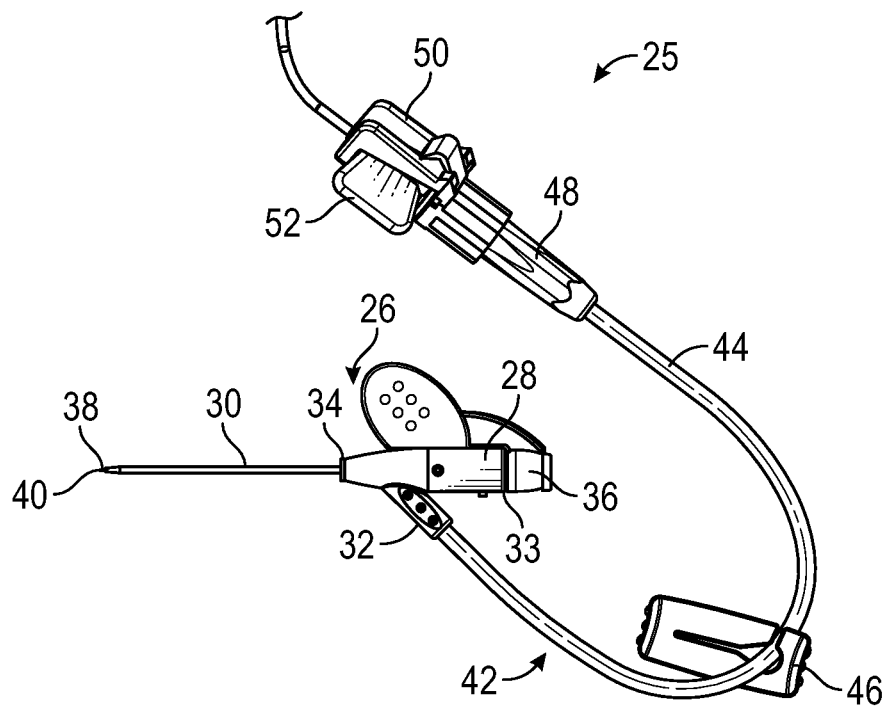
FIG. 2A is an upper perspective view of an example catheter system, according to some embodiments.

Referring now to FIG. 2A, a catheter system 25 may include a catheter assembly 26. In some embodiments, the catheter assembly 26 may include a catheter adapter 28 and a catheter 30 extending distally from the catheter adapter 28. In some embodiments, the catheter adapter 28 may include a side port 32 in fluid communication with a lumen of the catheter adapter 28. In some embodiments, the catheter adapter 28 may include a proximal end 33, a distal end 34, and the lumen extending between the proximal end 33 and the distal end 34. In some embodiments, the catheter 30 may include a peripheral intravenous catheter ("PIVC"), a midline catheter, or a peripherally inserted central catheter ("PICC").

In some embodiments, the catheter assembly 26 may be removably coupled to a needle assembly, which may include a needle hub 36 and an introducer needle 38. In some embodiments, the introducer needle 38 may include a sharp distal tip 40. In some embodiments, a proximal end of the introducer needle 38 may be secured within the needle hub 36. In some embodiments, the introducer needle 38 may extend through the catheter 30 when the catheter assembly 26 is in an insertion position ready for insertion into vasculature of a patient, as illustrated, for example, in FIG. 2A. In some embodiments, in response to the introducer needle 38 being inserted into the vasculature of the patient, flashback of blood may flow through the sharp distal tip 40 of the introducer needle 38 and may be visible to a clinician between the introducer needle 38 and the catheter 30 and/or at another location within the catheter assembly 26.

In some embodiments, in response to confirmation via the blood flashback that the catheter 30 is positioned within vasculature of the patient, the needle assembly may be removed from the catheter assembly 26. In some embodiments, when the needle assembly is coupled to the catheter assembly 26, as illustrated, for example, in FIG. 2A, the introducer needle 38 of the needle assembly may extend through a septum disposed within the lumen of the catheter adapter 28.

In some embodiments, the catheter system 25 may include an extension set 42, which may include an extension tube 44 and a clamp 46. In some embodiments, a distal end of the extension tube 44 may be integrated with the catheter adapter 28, as illustrated, for example, in FIG. 2A. For example, the extension tube 44 may be integrated with the side port 32 of the catheter adapter 28. In some embodiments, the extension tube 44 may be removably coupled to the catheter adapter 28. In some embodiments, the clamp 46 may selectively close off the extension tube 44 to prevent blood or another fluid from flowing through the extension tube 44.

In some embodiments, the extension set 42 may include an adapter 48 coupled to a proximal end of the extension tube 44. In some embodiments, the adapter 48 may include a Y-adapter or another suitable connector. In some embodiments, a connector 50 may be coupled to the adapter 48. In some embodiments, the connector 50 may include a needleless connector or PRN adapter. In some embodiments, the adapter 48 and/or the connector 50 may be used to connect the catheter system 25 with a winged needle set 52 or another medical device for fluid administration or blood withdrawal.

Figure 2B:
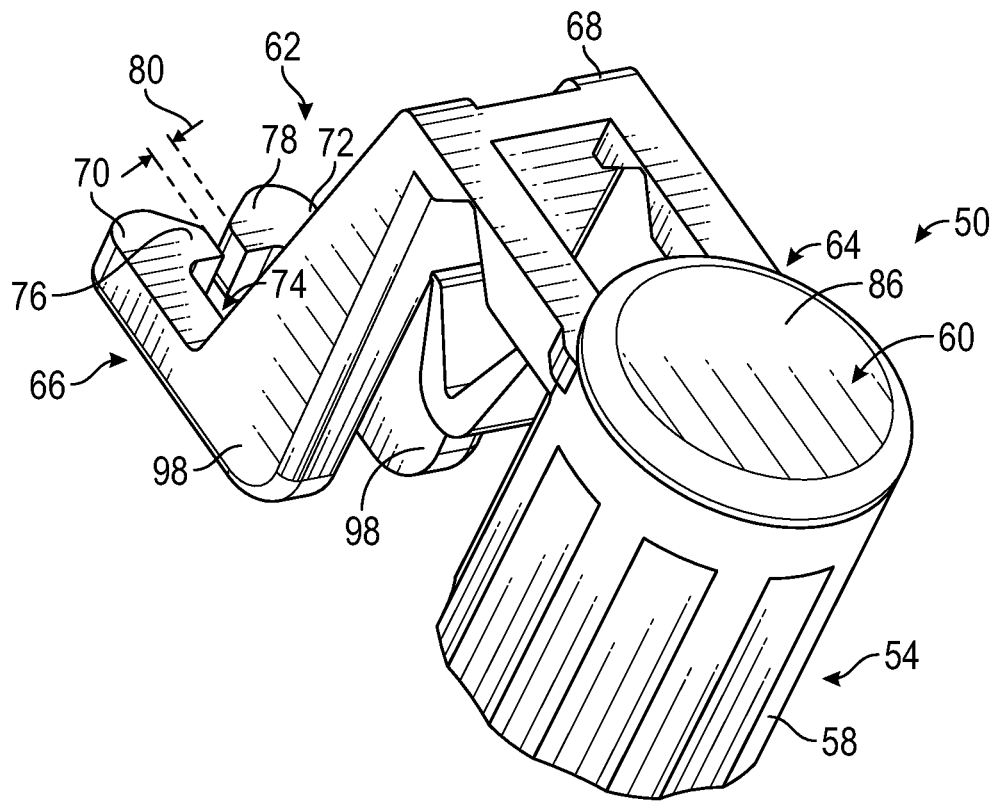
FIG. 2B is an upper perspective view of an example connector of the catheter system of FIG. 2A, illustrating an example hinge of the connector in an open position, according to some embodiments.
Figure 2C:
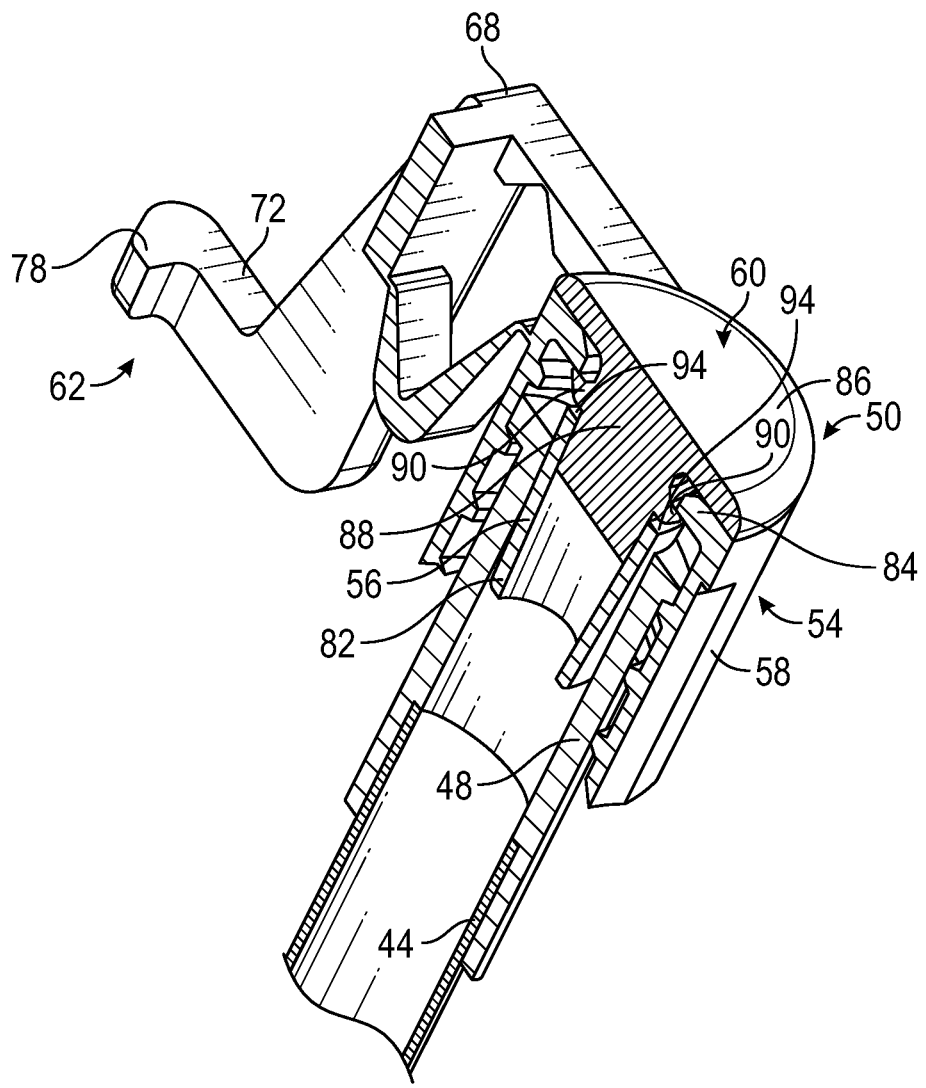
FIG. 2C is a cross-sectional view of the connector of FIG. 2B coupled to another connector of the catheter system of FIG. 2A, according to some embodiments.
Figure 2D:
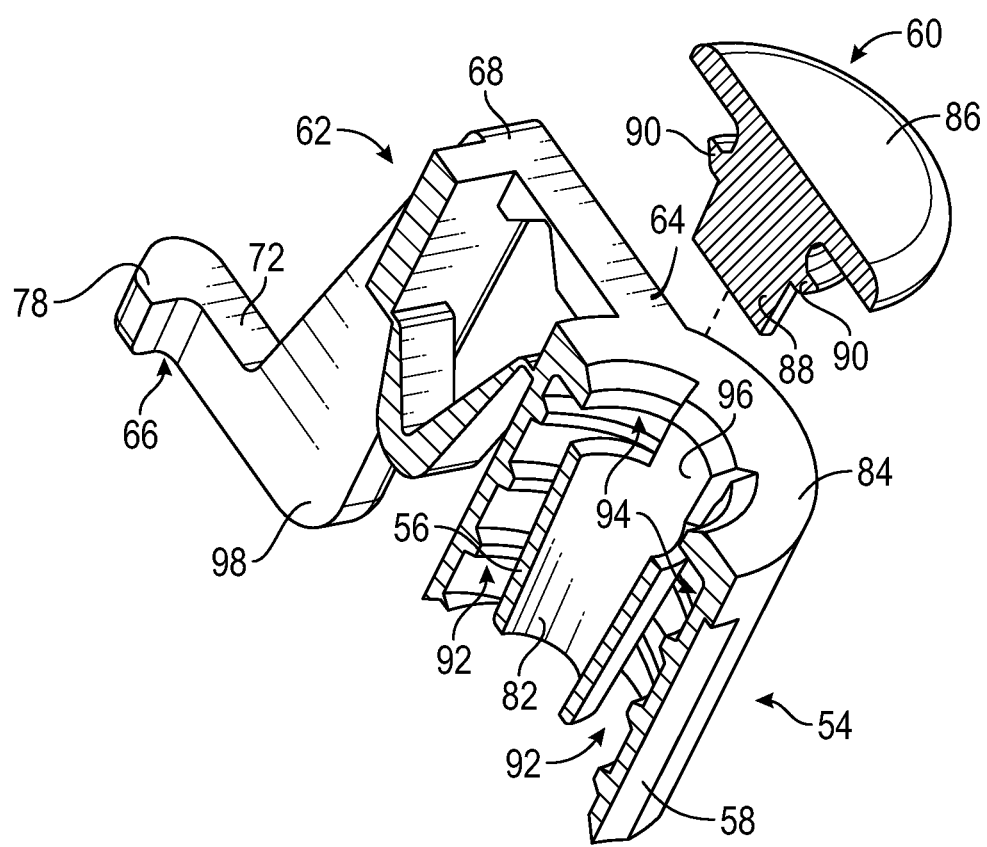
FIG. 2D is a cross-sectional view of the connector of FIG. 2B, illustrating an example septum removed, according to some embodiments.
Figure 2E:
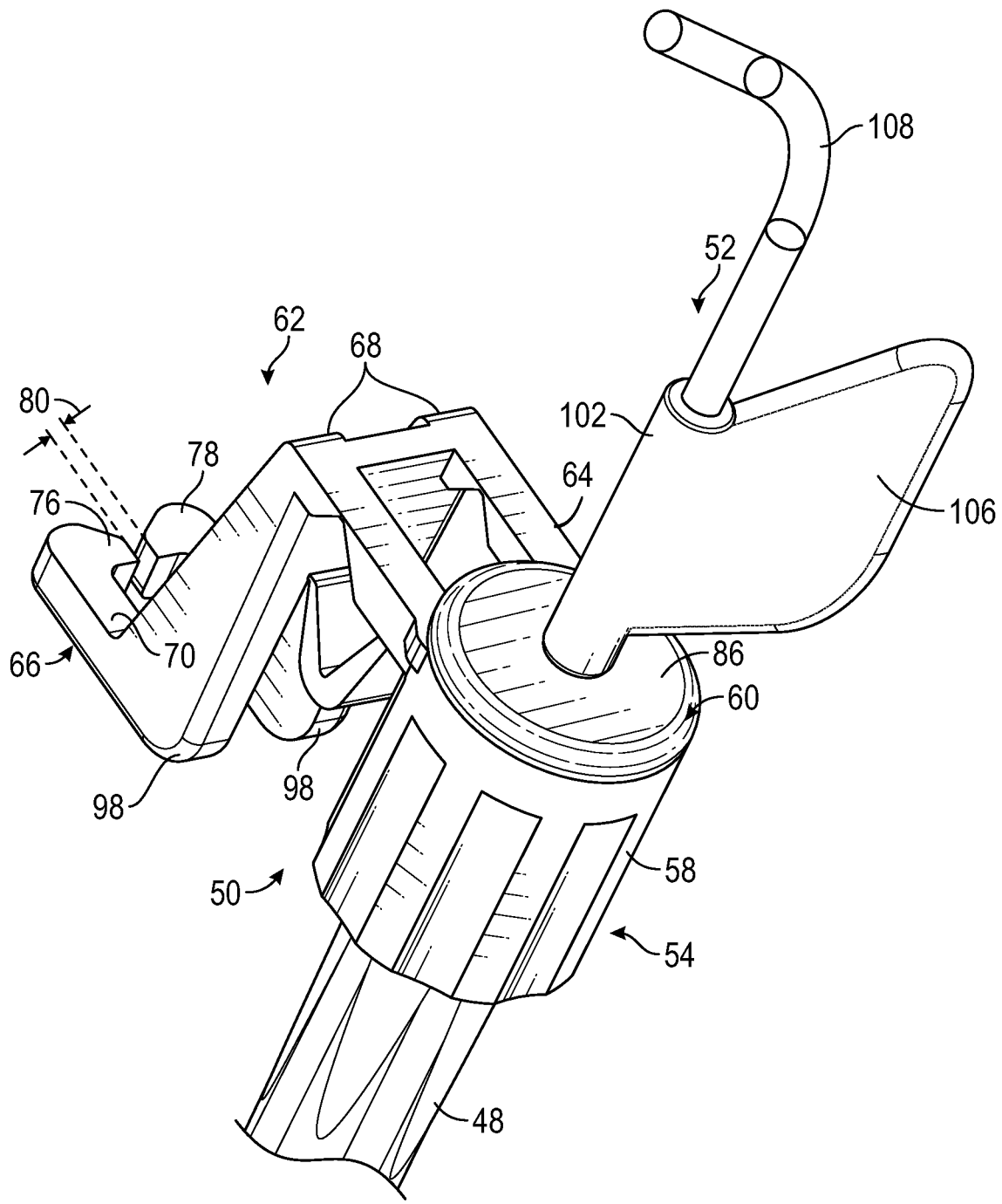
FIG. 2E is an upper perspective view of an example winged needle set inserted into the connector of FIG. 2B, according to some embodiments.

Referring now to FIGS. 2B-2D, in some embodiments, the connector 50 may include a male luer lock 54. In some embodiments, the male luer lock 54 may include a tapered male discharge nozzle 56 and a locking ring 58 surrounding the tapered male discharge nozzle 56. In some embodiments, the locking ring 58 may be internally threaded.

In some embodiments, the connector 50 may include a septum 60 configured to prevent flow through the tapered male discharge nozzle 56. In some embodiments, the connector 50 may include an arm 62, which may include a first end 64, a second end 66, and a hinge portion 68 disposed between the first end 64 and the second end 66. In some embodiments, the hinge portion 68 may include a living hinge, which may reduce a number of components and cost of the connector 50. In some embodiments, the hinge portion 68 may include another suitable type of hinge. In some embodiments, the first end 64 may be coupled to the male luer lock 54.

In some embodiments, the second end 66 of the arm 62 may include a first prong 70, a second prong 72, and an opening 74 disposed between the first prong 70 and the second prong 72. In some embodiments, the first prong 70 may include a first protrusion 76 and/or the second prong 72 may include a second protrusion 78. In some embodiments, a portion of the opening 74 between the first protrusion 76 and the second protrusion 78 may include a narrowed diameter 80, which may be less than a diameter 81 of the opening 74 (illustrated, for example, in FIG. 2F) closer to the hinge portion 68.

In some embodiments, the locking ring 58 may extend beyond a free end 82 of the tapered male discharge nozzle 56, which may reduce a risk of bacterial contamination of the tapered male discharge nozzle 56. In some embodiments, the locking ring 58 may include a flange 84. In some embodiments, the septum 60 may include a cap 86 and/or a stem 88 extending from the cap 86. In some embodiments, the stem 88 may extend into the tapered male discharge nozzle 56 and/or the cap 86 may rest on the flange 84, which may facilitate securement of the septum 60 within the connector 50.

In some embodiments, the stem 88 may include one or more protrusions 90. In some embodiments, the tapered male discharge nozzle 56 may be spaced apart from the locking ring 58 by a cavity 92, which may be annular. In some embodiments, the connector 50 may include one or more apertures 94, which may connect an interior of the tapered male discharge nozzle 56 with the cavity 92. In some embodiments, the protrusions 90 of the septum 60 may be disposed within the apertures 94, which may facilitate securement of the septum 60 within the connector 50. In some embodiments, the protrusions 90 may be disposed between the flange 84 and the tapered male discharge nozzle 56.

In some embodiments, the tapered male discharge nozzle 56 may be coupled to the locking ring 58 at an attachment portion 96. In some embodiments, the apertures 94 may be proximate the attachment portion 96. In some embodiments, the flange 84 may be disposed between the cap 86 and the protrusions 90 and/or may contact the protrusions 90. In some embodiments, the protrusions 90 may extend into the cavity 92 and/or contact an internal surface of the locking ring 58.

In some embodiments, the second end 66 of the arm 62 may include one or more shoulders 98, which may be angled. In some embodiments, the shoulders 98 may be angled at 90 degrees, which may facilitate securement of the winged needle set, or another suitable angle.

Figure 2F:
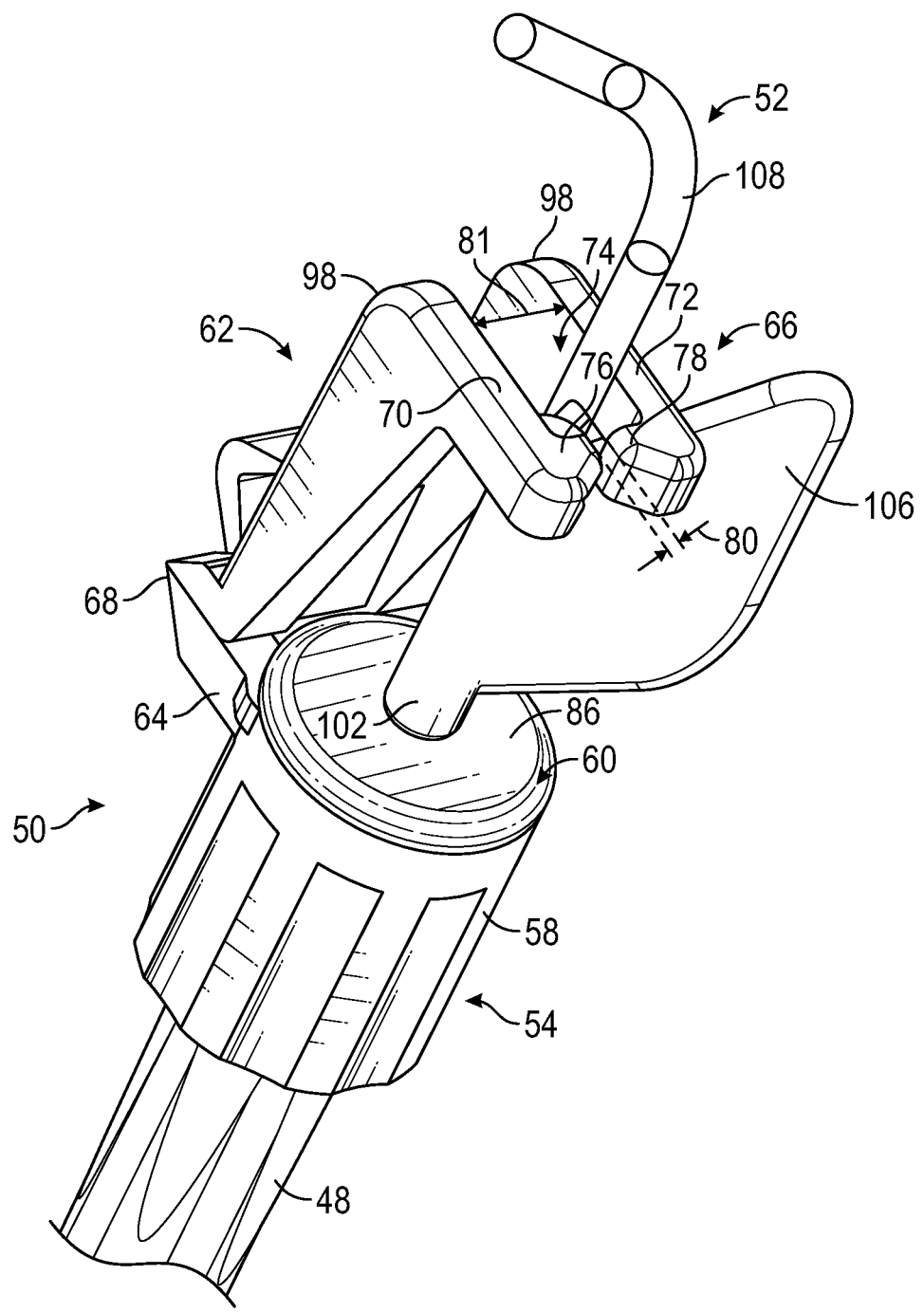
FIG. 2F is an upper perspective view of the winged needle set inserted into the connector of FIG. 2B, illustrating the hinge in a closed position, according to some embodiments.
Figure 2G:
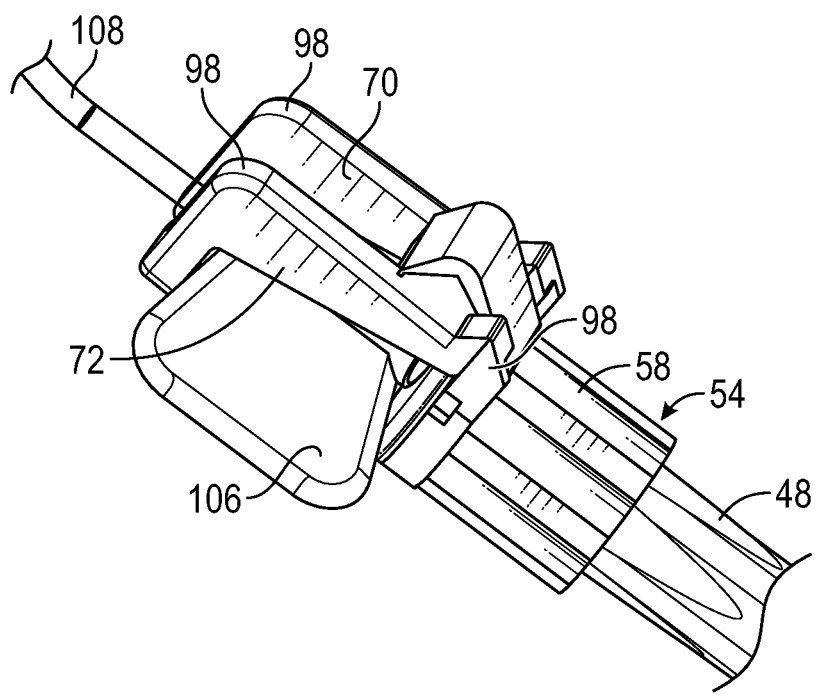
FIG. 2G is a lower perspective view of the winged needle set inserted into the connector of FIG. 2B, illustrating the hinge in the closed position, according to some embodiments.
Figure 2H:
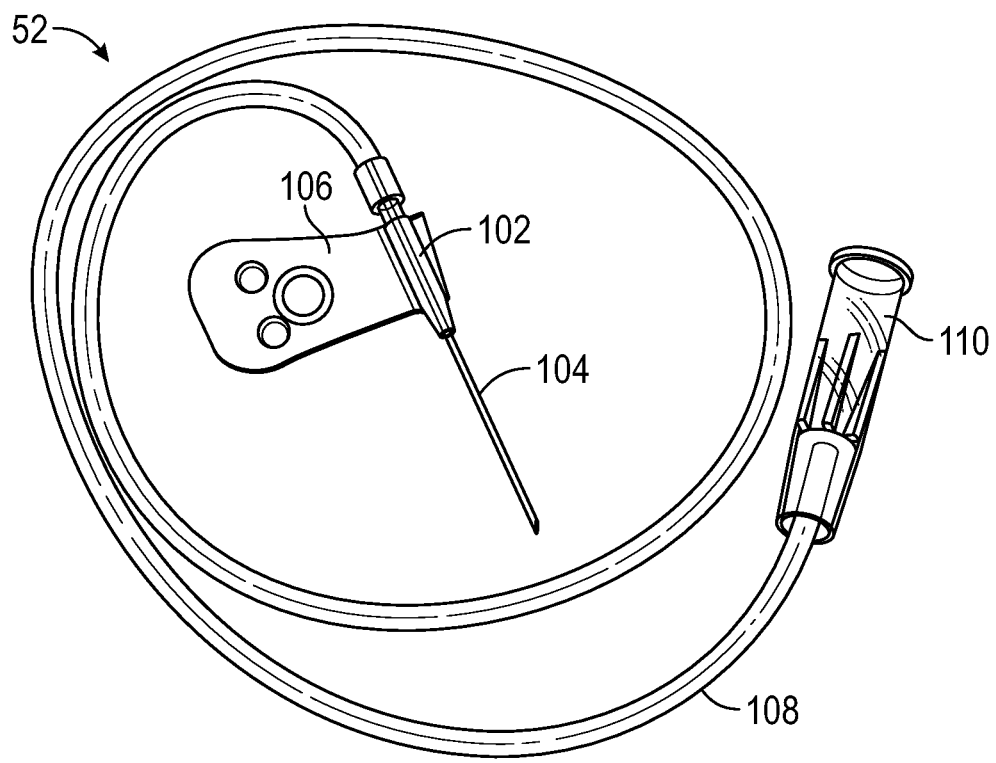
FIG. 2H is an upper perspective view of the winged needle set, according to some embodiments.

Referring now to FIGS. 2F-2H, in some embodiments, the opening 74 may be configured to receive a winged needle set 52. In some embodiments, in response to the hinge portion 68 moving from an open position, illustrated in FIGS. 2B-2E, for example, to a closed position, illustrated in FIGS. 2F-2G, for example, the arm 62 may be configured to secure the winged needle set 52 to the connector 50. In some embodiments, the winged needle set 52 may include a hub 102, a needle 104 secured within the hub 102, and one or more wings 106 extending outwardly from the hub 102.

In some embodiments, the opening 74 may be aligned with the tapered male discharge nozzle 56 in response to the hinge portion 68 being disposed in the closed position such that the winged needle set 52 may extend straight through the connector 50.

In some embodiments, the winged needle set 52 may be inserted through the septum 60 and into the tapered male discharge nozzle 56 after the connector 50 is coupled to a catheter assembly. In some embodiments, the hinge portion 68 may be moved by the clinician from the open position to the closed position by moving the second end 66 from an outer position to an inner position. In some embodiments, in response to the hinge portion 68 being in the closed position, the one or more wings 106 of the winged needle set 52 may be secured between the second end 66 and the septum 60.

In some embodiments, the winged needle set 52 may extend or be pushed through the opening 74 in response to the hinge portion 68 being in the closed position. In some embodiments, moving the hinge portion 68 from the open position to the closed position may include moving a portion of the winged needle set 52 through the narrowed diameter. In some embodiments, the first prong 70 and/or the second prong 72 may be formed of a resilient material. In some embodiments, the first prong 70 and the second prong 72 may be biased outwardly as the winged needle set 52 moves through the narrowed diameter 80, and after the winged needle set 52 is moved through the narrowed diameter 80, the first prong 70 and the second prong 72 may return inwardly, trapping the winged needle set 52. In some embodiments, one or more of the following may be monolithically formed as a single unit: the tapered male discharge nozzle 56, the locking ring 58, the attachment portion 96, the first end 64 of the arm 62, and the second end 66 of the arm 62.

Referring now to FIG. 2H, the winged needle set 52 is illustrated, according to some embodiments. In some embodiments, a first end of an extension tube 108 may be coupled to the hub 102. In some embodiments, a second end of the extension tube 108 may include an adapter 110, which may be configured to couple to an infusion or blood withdrawal device. In some embodiments, the needle 104 may be constructed of metal or another suitable material.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A connector to secure a winged needle set to a catheter assembly, the connector comprising:
   a male luer lock, comprising a tapered male discharge nozzle and a locking ring surrounding the tapered male discharge nozzle, wherein the locking ring comprises internal threads;
   a septum configured to prevent flow through the tapered male discharge nozzle; and
   an arm, comprising a first end, a second end, and a hinge portion disposed between the first end and the second end, wherein the first end is coupled to the male luer lock, wherein in response to the hinge portion moving from an open position to a closed position, the arm is configured to secure the winged needle set to the connector, wherein the second end comprises a first prong, a second prong, and an opening disposed between the first prong and the second prong, wherein the first prong comprises a first protrusion and the second prong comprises a second protrusion, wherein a portion of the opening between the first protrusion and the second protrusion includes a diameter, wherein the first prong and the second prong are constructed of a resilient material and configured to bias outwardly when the winged needle set moves through the diameter, wherein the locking ring comprises a flange, wherein the septum comprises a cap and a stem extending from the cap, wherein the stem extends into the tapered male discharge nozzle, wherein the cap rests on the flange, wherein the stem comprises a plurality of protrusions, wherein the tapered male discharge nozzle is spaced apart from the locking ring by a cavity proximate the internal threads, further comprising a plurality of apertures connecting an interior of the tapered male discharge nozzle with the cavity, wherein the plurality of protrusions of the septum are disposed within the plurality of apertures.

2. The connector of claim 1, wherein the opening is aligned with the tapered male discharge nozzle in response to the hinge portion being disposed in the closed position.

3. The connector of claim 1, wherein the diameter is narrower than a diameter of another portion of the opening disposed between the first prong and the second prong.

4. The connector of claim 1, wherein the hinge portion comprises a living hinge.

5. The connector of claim 1, wherein the locking ring extends beyond an end of the tapered male discharge nozzle.

6. The connector of claim 1, wherein the tapered male discharge nozzle is coupled to the locking ring at an attachment portion, wherein the plurality of apertures are proximate the attachment portion.

7. The connector of claim 1, wherein the flange is disposed between the cap and the plurality of protrusions and contacts the plurality of protrusions.

8. A medical connector, comprising:
a male luer lock, comprising a tapered male discharge nozzle and a locking ring surrounding the tapered male discharge nozzle, wherein the locking ring comprises internal threads; and
a septum configured to prevent flow through the tapered male discharge nozzle,
wherein the locking ring comprises a flange, wherein the septum comprises a cap and a stem extending from the cap, wherein the stem extends into the tapered male discharge nozzle, wherein the cap rests on the flange, wherein the stem comprises a plurality of protrusions, wherein the tapered male discharge nozzle is spaced apart from the locking ring by a cavity proximate the internal threads, further comprising a plurality of apertures connecting an interior of the tapered male discharge nozzle with the cavity, wherein the plurality of protrusions of the septum are disposed within the plurality of apertures.

9. A method of securing a winged needle set to a catheter assembly, comprising:

coupling a connector to a catheter assembly, wherein the connector comprises:
a male luer lock, comprising a tapered male discharge nozzle and a locking ring surrounding the tapered male discharge nozzle, wherein the locking ring is internally threaded;
a septum configured to prevent flow through the tapered male discharge nozzle; and
an arm, comprising a first end coupled to the male luer lock, a second end, and a hinge portion disposed between the first end and the second end, wherein the second end comprises a first prong, a second prong, and an opening disposed between the first prong and the second prong, wherein the first prong comprises a first protrusion and the second prong comprises a second protrusion, wherein a portion of the opening between the first protrusion and the second protrusion includes a diameter, wherein the first prong and the second prong are constructed of a resilient material;
inserting the winged needle set through the septum and into the tapered male discharge nozzle, wherein the winged needle set comprises a hub, a needle secured within the hub, and a wing extending outwardly from the hub; and
moving the hinge portion from an open position to a closed position, wherein in response to moving the hinge portion from the open position to the closed position, the first prong and the second prong are biased outwardly and a portion of the winged needle set moves through the diameter, wherein in response to the hinge portion being in the closed position, the wing of the winged needle set is disposed between the second end and the septum,
wherein the locking ring comprises a flange, wherein the septum comprises a cap and a stem extending from the cap, wherein the stem extends into the tapered male discharge nozzle, wherein the cap rests on the flange, wherein the stem comprises a plurality of protrusions, wherein the tapered male discharge nozzle is spaced apart from the locking ring by a cavity, further comprising a plurality of apertures connecting an interior of the tapered male discharge nozzle with the cavity, wherein the plurality of protrusions of the septum are disposed within the plurality of apertures.

10. The method of claim 9, wherein the winged needle set extends through the opening in response to the hinge portion being in a closed position.

11. The method of claim 9, wherein a diameter of the portion of the winged needle set is greater than the diameter of the portion of the opening between the first protrusion and the second protrusion.

12. The method of claim 9, wherein the hinge portion comprises a living hinge.

13. The method of claim 9, wherein the locking ring extends beyond an end of the tapered male discharge nozzle.

14. The method of claim 9, wherein the tapered male discharge nozzle is coupled to the locking ring at an attachment portion, wherein the plurality of apertures are proximate the attachment portion.

15. The method of claim 9, wherein the flange is disposed between the cap and the plurality of protrusions and contacts the plurality of protrusions.

* * * * *